United States Patent [19]

Moon

[11] 3,935,316

[45] Jan. 27, 1976

[54] METHOD OF USE AND FORMULATIONS

[75] Inventor: Malcolm W. Moon, Kalamazoo, Mich.

[73] Assignee: The Upjohn Company, Kalamazoo, Mich.

[22] Filed: Jan. 2, 1975

[21] Appl. No.: 537,836

[52] U.S. Cl. ................................................ 424/327
[51] Int. Cl.² ........................................ A61K 31/15
[58] Field of Search ..................................... 424/327

[56] References Cited
UNITED STATES PATENTS 3,786,131  1/1974  Buchel et al. ................... 424/327 X 3,824,233  7/1974  Friedman ........................ 424/327 X

*Primary Examiner*—Frederick E. Waddell
*Attorney, Agent, or Firm*—John J. Killinger; Roman Saliwanchik

[57] ABSTRACT

A new method for controlling parasitic worms in animals is described. The method employs a new chemical compound: 3-phenylpyruvoyl chloride 1-phenylhydrazone. Formulations of the compound with diluent carriers and adjuvants are discussed and exemplified. A synthesis of the compound is described.

7 Claims, No Drawings

METHOD OF USE AND FORMULATIONS

SUMMARY OF THE INVENTION

This invention pertains to a new method and new formulations for killing and controlling parasitic worms in animals. The invention is more particularly directed to the method and formulations for killing and controlling parasitic worms in animals with the new compound 3-phenylpyruvoyl chloride 1-phenylhydrazone. Preparation of the compound was first described in U.S. Pat. application Ser. No. 93,496, filed Nov. 27, 1970, now abandoned, wherein the compound was disclosed as an intermediate.

When a sample of the new compound was pulverized to a powder, a 3.0 gm. portion was filled into a gelatin capsule, and the capsule was administered orally to a naturally worm-infected wether weighing 30.0 kg., there was a significant reduction in the number of worm ova excreted. These results show utility as an anthelmintic. This anthelmintic activity was not previously known for this compound.

DETAILED DESCRIPTION OF THE INVENTION

The new compound 3-phenylpyruvoyl chloride 1-phenylhydrazone has the empirical formula, $C_{15}H_{13}ClN_2O$, and the structural formula:

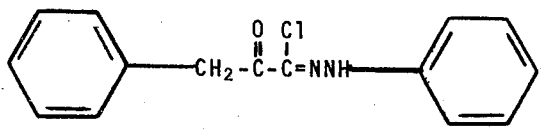

I

It can be prepared by conventional methods. For example, one can react phenylpyruvaldehyde with phenylhydrazine to obtain the prospective phenylhydrazone which is then chlorinated.

A perhaps better approach in order to avoid overchlorination complications attending the chlorination, is to start with phenylpyruvoyl chloride and react it with phenylhydrazine to obtain the corresponding phenylpyruvic acid phenylhydrazide.

The phenylpyruvic acid phenylhydrazide is then reacted with phosphorus pentachloride to produce the corresponding phenylpyruvoyl chloride (dichlorophosphinyl)phenylhydrazone. This intermediate is not separated, but is reacted with phenol, after the reaction mixture has been cooled to about 0° to 25°C., in order to obtain the desired 3-phenylpyruvoyl chloride 1-phenylhydrazone. For this purpose, three equivalents or more or phenol are used.

On the other hand, the desired compound, 3-phenylpyruvoyl chloride 1-phenylhydrazone, can be readily prepared by reacting a 1-phenyl-2,3,4-pentanetrione 3-phenylhydrazone with a loweralkyl, alkali, or alkaline earth metal hypochlorite followed by solvolysis of the intermediate 3-chloro-1-phenyl-3-phenylazo-2,4-pentanedione. According to this preferred method of preparation, the hypochlorite is a tert-alkyl hypochlorite, tert-butyl hypochlorite being especially preferred. This chlorinating:oxidizing agent is readily available.

The foregoing reaction is initiated with the 1-phenyl-2,3,4-pentanetrione 3-phenylhydrazone of the formula:

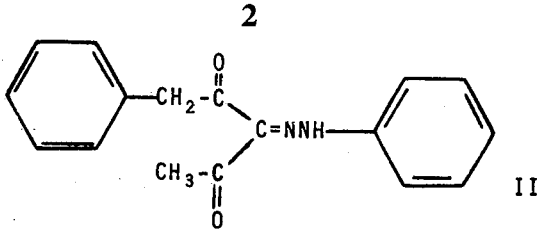

II

In consequence of the hypochlorite reaction step a 3-chloro-1-phenyl-3-phenylazo-2,4-pentanedione is obtained which has the following formula:

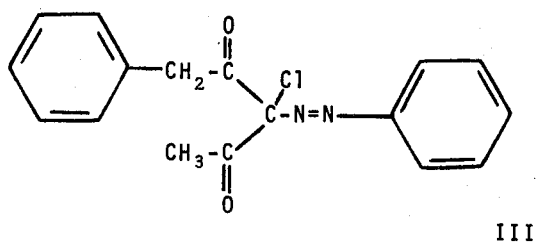

III

After solvolysis, which removes the unwanted acetyl group, the desired compound of Formula I, 3-phenylpyruvoyl chloride 1-phenylhydrazone is obtained by appropriate recovery and purification procedures.

In the foregoing reaction, an alkali metal hypochlorite, e.g., sodium or potassium hypochlorite can be used. Further alternatively, an alkaline earth metal hypochlorite, e.g., calcium hypochlorite can be used.

The reaction is effected by adding one equivalent (or an excess, if desired) of the chosen hypochlorite to an organic solution of the 1-phenyl-2,3,4-pentanetrione 3-phenylhydrazone. Chloroform is a preferred organic solvent medium but ethanol, benzene, toluene, or carbon tetrachloride could be used.

The alkyl hypochlorites are themselves liquids, and they are soluble in the named solvents. They react aggressively, and heat is produced by the reaction. Caution should be exercised.

On the other hand, alkaline earth metal hypochlorites are solids, and they should be dissolved in water before addition to the organic solution of triketone phenylhydrazone. In this case a two-phase aqueous:organic reaction medium is formed wherein the halogenated phenylazo compound remains in the organic phase.

The final solvolysis step which removes the unwanted acetyl group is advantageously effected with a mild reagent such as methanol or ethanol (preferred), dilute aqueous sodium hydroxide, or an amine, e.g., morpholine. In practice, the 3-chloro-1-phenyl-3-phenylazo-2,4-pentanedione is recovered from the reaction medium by conventional procedures such as physically separating the organic solvent layer and removing the solvent by evaporation. The residue thus obtained is then dissolved in methanol or ethanol for the solvolysis. When the solvolysis is complete, the desired 3-phenylpyruvoyl chloride 1-phenylhydrazone can be recovered from the alcoholic medium by well-known manipulative techniques such as filtration and solvent evaporation.

The starting 1-phenyl-2,3,4-pentanetrione-3-phenylhydrazone is prepared by reacting 1-phenyl-2,4-pentanedione with benzene diazonium chloride in accordance with methods known in the art, e.g., Chem. Ber. 21, p. 1702 (1888); 35, p. 2188 (1902). Those skilled in the art will recognize that 1,5-diphenyl-2,4-pentanedione could be used instead of 1-phenyl-2,4-pentanedione.

Likewise alternatively, the halogenation could precede the diazotization. For example, the 1-phenyl-2,4-pentanedione can be halogenated with the hypohalite reagent to form the 3-halo intermediate which can then be diazotized with benzene diazonium chloride to produce the desired 3-phenylpyruvoyl chloride-3-phenylhydrazone product.

PREPARATION 1

1-Phenyl-2,3,4-pentanetrione-3-phenylhydrazone

A quantity (27.0 gms., 0.15 mole) 1-phenyl-2,4-pentanedione was dissolved in a solvent medium consisting of 200 ml. water, 200 ml. ethanol, and 6 gms. sodium hydroxide. This reaction solution was added to 0.17 mole of benzene diazonium chloride present as a solute in 200 ml. of an aqueous solution prepared by mixing 87 ml. (1 mole) aniline, 500 ml. water, and 200 ml. concentrated hydrochloric acid; cooling to zero degrees C.; carefully adding an aqueous solution consisting of 69 gms. (1.0 mole) sodium nitrite, and 200 ml. water; and buffering with 272 gms. (2.0 moles) sodium acetate.

An oily precipitate formed which was collected on a filter and washed with ethanol. The washed precipitate weighed 21.0 gms. and melted at 101° to 104°C. After recrystallization from 200 ml. methanol, there was obtained 17.7 gms. of 1-phenyl 2,3,4-pentanetrione-3-phenylhydrazone having a melting point at 103° to 106°C.

Analysis Calcd. for: $C_{17}H_{16}N_2O_2$. C, 72.84; H, 5,71; N, 9.99. Found: C,72.93; H, 5.77; N, 10.12.

The following example is illustrative of the product and process of the present invention but is not to be construed as limiting.

EXAMPLE 1

Preparation of 3-Phenylpyruvoyl chloride 1-Phenylhydrazone

A mixture consisting of 2.8 gms. (0.01 mole) 1-phenyl-2,3,4-pentanetrione-3-phenylhydrazone (Preparation 1, above), 15 ml. chloroform, and 1.4 ml. tertbutyl hypochlorite was held at 25°C. for 4 hours. The volatile components were then removed by evaporation under reduced pressure. The resulting oil was mixed with 15 ml. methanol, and the mixture was heated to 40°C. for 1 hour. After seeding the cooled reaction mixture there was obtained 1.8 gms. of 3-phenylpyruvoyl chloride 1-phenylhydrazone that melted at 130°C. to 136°C.

The foregoing procedure was repeated, but using 12.1 gms. 1-phenyl-2,3,4-pentanetrione-3-phenylhydrazone, 100 ml. chloroform, and 6 ml. tert-butyl hypochlorite. Upon recrystallization from 100 ml. methanol there was obtained 6.3 gms. of compound having a melting point at 132° to 134°C.

Analysis Calcd. for: $C_{15}H_{13}ClN_2O$. C, 66.05; H, 4.80; Cl, 13.00; N, 10.27 Found: C, 66.63; H, 5.08; Cl, 12.87; N, 9.45, 9.27.

The 3-phenylpyruvoyl chloride 1-phenylhydrazone compound thus prepared, as above, was discovered to be active against worms, particularly parasitic worms, e.g. Haemonchus and Ostertagia in animals. The proof of the anthelmintic activity of the compound was obtained by administering 3.0 gms. of the compound to a naturally worm-infected wether lamb weighing 30.0 kg. Prior to treatment the lamb was excreting very high numbers of worm eggs. After treatment with the stated dosage (100 mg./kg. of body weight) the numbers of worm eggs excreted were significantly reduced. This before and after difference in numbers of excreted worm eggs indicates that the compound in some way interfered with the worms in the intestinal tract of the lamb. The worms were either killed or metabolically damaged so that they no longer layed eggs. In either circumstance, there was a beneficial effect in controlling worms. The level of infectivity or reproductive vigor of the worms was reduced.

The compound is accordingly contemplated as an anthelmintic useful in bovines, equines, porcines, canines, felines, piscenes, aves, and other animals. In addition to the dosage of 100 mg./kg. in sheep, applicant contemplates dosage rates, depending upon various circumstances, of from 5.0 mg. to 800 mg. per kg. of body weight. A preferred, contemplated range of dosage rates is from 25 mg. to 400 mg. per kg. of body weight.

With regard to dosage rates, it should be noted that there can be advantages in a multiple dosing regimen as contrasted with the single dosage of the described test. In some instances is is convenient and advantageous to administer small dosages at frequent intervals. For example, a pet dog or cat and even a pony might be given a unit dosage of a discrete formulation (e.g., tablet, pill, capsule, or bolus) morning and evening over a period of one, two, or more days. In other instances, relatively continuous low level administration can be accomplished in a ration. Still other substantially obvious ways of utilizing the newly discovered anthelmintic activity of 3-phenylpyruvoyl chloride 1-phenylhydrazone can be recognized. Further illustratively, a worminfected animal can be drenched with a liquid unit dosage formulation, or a dosage can be administered in the food ration at feeding time. Parenteral injectables can also be used via subcutaneous route, for example.

The uncomplicated form (finely divided powder) and route of administration (orally) is convenient for the compound of this invention because it is a solid at ordinary room temperatures. The compound is not very soluble in water, but various known forms and routes of administration are contemplated as embodiments of this invention.

For example, the pure compound can be finely divided and mixed with a finely-divided solid diluent carrier if desired. Such finely-divided solid diluent carriers can include starches, e.g., corn starch; powdered lactose; powdered sucrose; talc; stearic acid; magnesium stearate; finely divided bentonite clays; vegetable gums; cellulosic products; and other materials of like kind. The active compound can be mixed with the diluent carrier in varying proportions from, for example, 0.001 per cent by weight to 90, 95, or more per cent. Mixtures of different diluent carriers can be used.

The 3-phenylpyruvoyl chloride 1-phenylhydrazone can be mixed with an animal ration so that it is administered at a low level, continuous dosage rate depending upon how much ration the animal consumes. Since the chlorine atom on the carbonyl carbon is substantially reactive, any free amino groups or possible enzymes present in the feedstuffs might cause degradation of the compound. Ground feed mixes are expecially likely to result in degradation, but whole grain animal feedstuffs such as whole corn and oats, will not likely cause the problem. It is thus recognized that advantageous administration to animals via their rations will probably require some conventional coating techniques, judgment, and evaluation.

On the other hand, the compound can be formulated in stable powders or granules for mixing in an amount of ration for a single feeding or even in an amount for a whole day. In this way (premixes) degradation can be avoided and therapeutic efficacy in a whole herd or flock can be obtained.

If desired, a granular premix formulation can also be coated so as to protect and preserve the active compound from degradative reactions. When so coated and protected, 3-phenylpyruvoyl chloride 1-phenylhydrazone can be mixed in a swine ration at a concentration of 0.2 per cent, for example. This medicated feed can be administered for an interval of time during which anthelmintic medication is indicated. At this concentration a feeder pig will receive a dosage of about 100 mg. per kg. of body weight per day in its daily ration.

In preparing stable powders or granules indicated above, or in preparing mixtures of the active compound with finely divided solid diluent carrier as mentioned earlier, adjuvants may be advantageously included. Representative adjuvants include water, alcohols, protein solutions or suspensions like skimmed milk; edible oils, sugar solutions, e.g., syrups, and organic adjuvants such as propylene glycols, sorbitol, glycerol, diethyl carbonate, and the like. These adjuvants might contribute qualities of texture, flavor, body and stability that will enhance the action of the active compound.

The solid carrier formulations for the invention are conveniently prepared indiscrete unit dosage forms, to facilitate administration to animals. Accordingly, several large boluses (about 20 gms. weight) amounting to about 54 gms. of active compound would be required for a single dosage to a 900 lbs. horse at a dosage rate of 50 mg./kg. of body weight. Similarly, a 60 lbs. lamb at a dosage rate of 100 mg./kg. of body weight would require a pill, tablet, capsule, or bolus containing about 2.7 gms. of active compound. A small dog, on the other hand, weighing about 20 lbs. would require a total dosage of about 225 mg. at a dosage rate of 25 mg./kg. of body weight. The solid, unit dosage forms can be conveniently prepared in various sizes and concentrations of active ingredient, to accomodate treatment of the various sizes of animals that are parasitized by worms.

Liquid formulations of 3-phenylpyruvoyl 1-phenylhydrazone can also be used for effecting control of worms in animals. Since the compound is insoluble in water, aqueous suspensions can be used. Such may include isotonic saline suspensions. Oil solutions and suspensions, and oil:water emulsions can also be used.

Aqueous suspensions are obtained by dispersing the compound in water, advantageously including a suitable surface-active dispersing agent such as cationic, anionic, or non-ionic surface-active agents. Representative suitable ones are polyoxyalkylene derivatives of fatty alcohols and of sorbitan esters, and glycerol and sorbitan esters of fatty acids. Various dispersing or suspending agents can be included and representative ones are synthetic and natural gums, tragacanth, acacia, alginate, dextran, gelatin, sodium carboxymethylcellulose, methylcellulose, polyvinylpyrrolidone, and the like. The proportion of the active compound in the aqueous suspensions of the invention can vary from about 1 to about 20% or more. The proportion is not critical but is necessarily dependent upon the efficiency of suspension. Slurries are contemplated.

In accordance with the method and formulation contemplations of this invention a unit dosage formulation may be a liquid form for administration to an animal via stomach tube or as a drench. In general, the concept of treatment is to administer a measured dosage of a liquid formulation so that desired efficacy is achieved. The liquid dosage is manually administered into the stomach of the animal where it acts if worms are present there. Further anthelmintic action is continued in the intestines as the compound is passed along by normal body processes.

EXAMPLE 2

A representative drench suspension is prepared by mixing the following amounts and kinds of ingredients:

3-phenylpyruvoly chloride 1-phenylhydrazone 80 gms.

Benzalkonium chloride (12.8% aqueous solution) 20 ml.

Antifoam AF (emulsion of dimethylpolysiloxane, available from Dow-Corning 2 gms.

Hydroxyethyl cellulose (WP 4400, Union Carbide Chemical Company) 12.5 gms.

Water q.s. to 1 liter

The described one liter of drench suspension contains 8.0 grams of active agent for each 100 ml., so a practical volume unit dosage for a sheep of from 25 to 100 ml. will contain from 2.0 to 8.0 grams of active compound. A 30 to 40 lb. lamb is advantageously treated with a 35 ml. (2.8 gms.) unit dosage at the rate of 175 mg./kg. of body weight. A 150 to 160 lb. ewe on the other hand is treated with a 100 ml. unit dosage at the rate of 111 mg./kg. of body weight. Higher or lower dosages can be administered depending upon the degree of infection, the health of the sheep, and their size. More concentrated or less concentrated drench suspensions can be formulated depending upon equipment for administration and desirability of more or less bulk. Other suspending agents and adjuvants can also be used if desired.

Oil solutions are prepared by mixing the active compound and oil, e.g., an edible oil such as cotton seed oil, peanut oil, coconut oil, modified soybean oil, and sesame oil. Usually, solubility in oil will be limited and oil suspensions can be prepared by mixing additional finely divided compound in the oil.

Oil in water emulsions are prepared by mixing and dispersing an oil solution or suspension of the active compound in water preferably aided by surface-active agents and dispersing or suspending agents as indicated above.

In general, the formulations of this invention are administered to animals so as to achieve therapeutic or prophylactic levels of the active compound. At present, it is known that 100 mg./kg. of body weight in lambs will effectively combat a wide variety of parasitic worms. Lower effective dosages are contemplated, e.g., in the range of 25 to 75 mg./kg. of body weight.

In some circumstances, the concentration of 3-phenylpyruvoyl 1-phenylhydrazone in the formulation selected for administration is not critical. That is to say, one can administer a larger quantity of a formulation having a relatively low concentration of active ingredient and achieve the same therapeutic or prophylactic result as a relatively smaller quantity of a more concentrated formulation.

The formulations of the invention can be prepared in discrete unit dosage forms such as capsules pills, tablets, wafers, boluses, cachets, and vials. The objective of unit dosage forms is to have the active compound present in such amount in a separable entity that it will be convenient for those of ordinary skill in the therapeutic art to administer an effective dosage but not overdose and thus waste active ingredient or possibly compromise the health of a treated animal. A unit dosage can contain appropriately from 10 mg. to 300 gms. of compound per unit.

I claim:

1. The method for therapeutically and prophylactically controlling parasitic Haemonchus or Ostertagia worms in animals which comprises administering orally or parenterally to animals an effective anthelmintic dosage of 3-phenylpyruvoyl chloride 1-phenylhydrazone.

2. The method according to claim 1 wherein the dosage is from 5 mg. to 800 mg. per kg. of body weight.

3. The method according to claim 2 wherein the dosage is from 25 mg. to 400 mg.

4. The method according to claim 3 wherein a sheep is given a dosage of from 25 mg. to 400 mg. per kg. of body weight.

5. The method according to claim 1 wherein the animals are sheep.

6. Unit dosage formulations for administration to animals in therapeutically and prophylactically effective amounts for thus controlling parasitic Haemonchus or Ostertagia worms in the animals which comprise as the essential active ingredient from 10 mg. to 300 grams of 3-phenylpyruvoyl chloride 1-phenylhydrazone and a physiologically acceptable carrier.

7. A discrete unit dosage formulation according to claim 6 wherein a capsule, tablet, pill, bolus, or cachet form is prepared.

* * * * *